United States Patent [19]

Carme et al.

[11] Patent Number: 4,833,719
[45] Date of Patent: May 23, 1989

[54] METHOD AND APPARATUS FOR ATTENTUATING EXTERNAL ORIGIN NOISE REACHING THE EARDRUM, AND FOR IMPROVING INTELLIGIBILITY OF ELECTRO-ACOUSTIC COMMUNICATIONS

[75] Inventors: Christian E. Carme; Alain R. Roure, both of Marseille, France

[73] Assignee: Centre National de la Recherche Scientifique, Paris, France

[21] Appl. No.: 110,699

[22] PCT Filed: Mar. 6, 1987

[86] PCT No.: PCT/FR87/00056
§ 371 Date: Sep. 23, 1987
§ 102(e) Date: Sep. 23, 1987

[87] PCT Pub. No.: WO87/05430
PCT Pub. Date: Sep. 11, 1987

[30] Foreign Application Priority Data

Mar. 7, 1986 [FR] France .................. 86 03394

[51] Int. Cl.⁴ .................................. A61F 11/02
[52] U.S. Cl. ............................. 381/72; 381/94
[58] Field of Search .............. 381/72, 74, 25, 83, 381/93, 68.2, 68.4, 94

[56] References Cited

U.S. PATENT DOCUMENTS 4,494,074 1/1985 Bose .......................... 330/109

FOREIGN PATENT DOCUMENTS 2925134 8/1981 Fed. Rep. of Germany .
2160070 12/1985 United Kingdom .

Primary Examiner—Forester W. Isen
Attorney, Agent, or Firm—Balogh, Osann, Kramer, Dvorak, Genova & Traub

[57] ABSTRACT

The invention relates to a method and to apparatus for attenuating externally originating noise reaching the eardrum while still enabling communication via an electro-acoustic path. Apparatus according to the invention comprises passive attenuation means disposed about each ear and delimiting a cavity (10). In addition it includes active attenuation means comprising a loudspeaker (6) placed inside the cavity (10) and a microphone (8) placed in the external ear duct or at the inlet thereto, said loudspeaker and microphone being interconnected by a constant gain amplifier (11) and an active analog filter (12) of the polynomial type, with the passive components thereof being designed to provide a given transfer function. One application lies in the construction of protective headsets fitted with incorporated loudspeakers enabling electro-acoustic communication.

19 Claims, 5 Drawing Sheets

METHOD AND APPARATUS FOR ATTENTUATING EXTERNAL ORIGIN NOISE REACHING THE EARDRUM, AND FOR IMPROVING INTELLIGIBILITY OF ELECTRO-ACOUSTIC COMMUNICATIONS

The present invention relates to methods and apparatuses for attenuating external origin noise reaching the eardrum, and for improving the intelligibility of electro-acoustic communications.

The technical field of the invention is the construction of acoustical protectors for the ear.

Passive soundproofing means are known such as headsets or earmuffs placed over the ears to protect persons required to remain in very noisy surroundings. Such means are used, for example, by workers working in certain types of workshop, by the drivers of very noisy vehicles (airplanes, tanks, . . .), by ground personnel at airports, etc. . .

Such headsets generally comprise a muff of absorbent material which envelops the ear.

In this type of sound insulation, incident airbourne sound waves are attenuated by reflection and by absorption in the mass of the material which is acting as a passive screen.

Experience shows that passive soundproofing means are not very effective for low frequency sounds, and in particular in the frequency range below 500 Hz. In order to be effective at such frequencies, such headsets would require prohibitive densities or thicknesses of material.

Sound insulating headsets are known which additionally include a loudspeaker or an electro-acoustic transducer incorporated inside each muff in order to allow the user to hear messages which are transmitted by the electro-acoustic means.

The problem to be solved is to improve the efficiency of headsets and other passive soundproofing means by adding apparatus thereto for improving the attenuation of sounds of external origin lying in the frequency range where the passive means is not very effective.

Apparatus known as an active acoustical attenuator is also known which serves to attenuate some sounds by making them interfere with other sounds which are set up in phase opposition to the sounds to be attenuated.

First attempts took place around 1953-1956 and have been described by Olson and May.

The active acoustical attenuator proposed by these authors comprises a microphone connected to a loudspeaker via an electronic amplifier in such a manner that the loudspeaker produces pressure within the cavity which opposes the pressure due to the incident wave picked up by the microphone. If the incident wave is random noise, the attenuation obtained by this method is not very good, and in addition this method gives rise to instabilities due to resonances at certain frequencies ("howlaround", or the Larsen effect).

In 1955-1956, Hawley and Simshauer published work inspired by Olson's work. In order to avoid resonances due to sound feedback, Hawley proposed making soundproofing headsets which attenuated only some kinds of unwanted noise, which was either in the form of pure harmonic sounds or else in the form of very narrowband noise. Such headsets can only attenuate noise of a form determined in advance and they do not attenuate noise lying in a wide frequency range.

At pages 399 and 403 of Inter Noise 1983, Chaplin and Smith describe an anti-noise device enabling harmonic sounds to be attenuated by making them interfere with a synchronous sound in phase opposition as generated by a synthesizer controlled by digital electronics. Such apparatus using a sound which is synchronous with the sounds to be attenuated can be used only for attenuating a noise made up of a pure frequency together with its harmonics. Any variations in the frequency of the sound must be slow in order to make it possible for the digital processing to correct the frequency of the feedback signal. The need for a synchronization signal means that a noise canceller must be provided for each source of noise. Digital electronics is complex and expensive to implement. This method is thus not usable for improving the efficiency of passive soundproofing means intended to be used in very noisy locations in sound fields essentially constituted by random noise.

French Pat. No. 75 34 024 (A.N.V.A.R.) describes active sound absorbing apparatus for attenuating plane sound waves propagating along a duct.

French Pat. No. 83 13 502 describes regulator apparatus for an electro-acoustic system in which a filter is incorporated between the pickup member and the loudspeaker, said filter having a transfer function which is the inverse of the transfer function of the assembly constituted by the loudspeakers and the room in which listening is taking place.

The filter used is a non-recursive programmable digital filter of the convolution type provided with an input sampler.

This patent also described means for attenuating noise propagating along a guide, which means comprise a microphone connected to a plurality of loudspeakers by an electronic system including a filter of the convolution digital filter type which causes the electrical signals to be appropriately filtered in order to minimize the noise.

The means described in these prior documents require major adaptation in order to be usable in combination with portable passive soundproofing means such as headsets or earplugs.

The latter prior document describes active acoustical attenuators each including a digital filter which provides a complex transfer function which is the inverse of the transfer function of an electro-acoustic system. Such a solution including a digital filter requires a processor unit to be used in real time and constitutes an expensive solution which is difficult to use with walkabout passive soundproofing means.

U.S. Pat. No. 4,494,074 (Bose) describes earphones including a microphone and an electro-acoustic transducer connected via a feedback loop including a preamplifier, a signal adder, compensation circuits including filters, and an amplifier for driving the transducer.

British Pat. No. GB-A-2 160 072 (Plessey) describes active noise attenuators associated with earphones. Each attenuator comprises a microphone connected to an electro-acoustic transducer via a feedback loop including an inverting amplifier.

German Pat. No. DE-A-2 925 134 (Sennheiser Electronic K.G.) describes active apparatus for providing protection against external noise, the apparatus comprising a microphone connected to an electro-acoustic emitter via a feedback loop shown diagrammatically, including an amplifier and optionally including an adjustable high-pass or low-pass filter.

Some of these prior documents mention the presence of a filter in the feedback loop, but none of them specifies how said filter is chosen and what transfer function it should have in order to obtain the best possible attenuation.

An aim of the present invention is to provide active attenuation means associated with means delimiting a cavity around the ear, said attenuation means including a filter whose transfer function is determined on the basis of the open loop transfer function of said cavity in such a manner as to obtain good active attenuation over a wide frequency range, and in particular including the low frequency sounds for which passive soundproofing devices are not very effective.

The method in accordance with the invention for attenuating external origin noise reaching the eardrum is of the type in which each ear is associated with passive soundproofing means which together delimit a cavity, with a microphone and an electro-acoustic transducer being disposed inside said cavity, said microphone and transducer being interconnected by a feedback loop including a constant gain amplifier and a filter to constitute an active soundproofer.

The aim of the invention is achieved by means of a method in which the transfer function $C(w)$ of the filter is a complex polynomial function and the open loop transfer function $H(w)$ of the assembly constituted by the transducer, the microphone, and the cavity delimited by said passive soundproofing means and the ear is measured, the coefficients of said polynomial function $C(w)$ then being calculated so that the product of the constant gain of said amplifier multiplied by the modulus of said open loop transfer function $|H(w)|$ and by the modulus of the transfer function of said filter $|C(w)|$ is much greater than unity over the range of frequencies where said passive soundproofing means is of low effectiveness while retaining stability in the feedback system.

Apparatus in accordance with the invention for attenuating external origin sounds comprises passive soundproofing means for delimiting a cavity around each ear and additionally comprises a microphone and an electro-acoustic transducer which are disposed inside said cavity and which are interconnected by a feedback loop including a constant gain amplifier and a filter with which they constitute an active sound attenuator.

The aim of the invention is achieved by means of apparatus in which the transfer function $C(w)$ of the filter is a complex polynomial function such as the product of the modulus $|C(w)|$ multiplied by the modulus $|H(w)|$ of the open loop transfer function and by the gain K of the amplifier is greater than unity throughout the range of the frequencies to be attenuated.

The invention provides means enabling the efficiency of headsets and other similar passive soundproofing means to be improved by associating them with an active sound attenuator including, in its feedback loop, a filter for optimizing the efficiency of the passive soundproofing means over a wide frequency range.

It is known that passive soundproofing means are poor attenuators of low frequency sounds, i.e. sounds at frequencies below 500 Hz, which sounds are very common in some noise, for example vehicle engine noise.

Apparatus in accordance with the invention improves sound attenuation, inter alia, by means of a feedback loop including a constant gain amplifier and a filter which is preferably an analog filter of the polynomial type whose components are designed so that the ratio between the total acoustic pressure inside the cavity and thus at the eardrum to the acoustic pressure due to external noise that has passed through the passive soundproofing means remains low over the entire range of frequencies that are to be attenuated.

The design of analog polynomial filters is a technique that is well known to the person skilled in the art.

The modulus of the overall transfer function of a feedback loop in accordance with the invention is equal to the product of the constant gain (K) of the amplifier multiplied by the modulus of the filter transfer function $|C(w)|$ and by the modulus of the open loop transfer function $|H(w)|$, i.e. as measured between the input to the transducer and the output from the microphone.

The modulus and the argument of the open loop transfer function $H(w)$ can be measured and plotted by injecting a white noise signal into the transducer input and by simultaneously applying said signal and the signal emitted by the microphone to a spectrum analyzer.

Given the modulus and the argument of the open loop transfer function of a passive attenuation means equipped with an electro-acoustic transducer and with a microphone having a given disposition, it is possible to calculate the values of passive components for a filter such that the modulus of the transfer function of the filter follows a given law over the frequency range to be attenuated while still satisfying the stability criterion so as to avoid producing any resonance due to "howl-around" or the Larsen effect.

Apparatus in accordance with the invention serves equally well for attenuating continuous noise and impulse noise, i.e. noise of the kind generated by shocks or detonations, giving an amplitude that varies very fast. This is made possible by the fact that the electronic processing takes place in real time.

The following description refers to the accompanying drawings which show non-limiting embodiments of the invention.

FIGS. 8 and 9 show specific embodiments of a filter.

FIG. 1 is a diagram showing apparatus in accordance with the invention placed over the ears of a subject for the purpose of attenuating external noise as perceived by the subject.

This apparatus comprises passive soundproofing means constituted, for example, by two muffs $1d$ and $1g$ which surround each ear and which are interconnected by a headband 2 in order to constitute a headset. The muffs $1d$ and $1g$ are applied against the sides of the head and together therewith they delimit respective cavities each enclosing a corresponding ear pinna. Each such cavity is closed and comprises two cavities: the first corresponding to the inside of the muff; and the second corresponding to the auditive cavity delimited by the pinna, the external ear duct, and the eardrum.

The muffs 1d and 1g constitute passive soundproofing apparatus for reflecting and absorbing a portion of the soundwaves, thereby attenuating the noise which reaches the ear. The muffs 1d and 1g may be replaced by any other passive soundproofing apparatus, for example by plugs placed at the entrance to each external ear duct. In this case, the closed cavity is constituted by a first half-open half-cavity comprising the earplugs and its miniaturized transducers, together with a second half-cavity which is constituted by the eardrum and the external ear duct.

Experience shows that passive soundproofing apparatus attenuates low frequency sound poorly.

Figure 1:
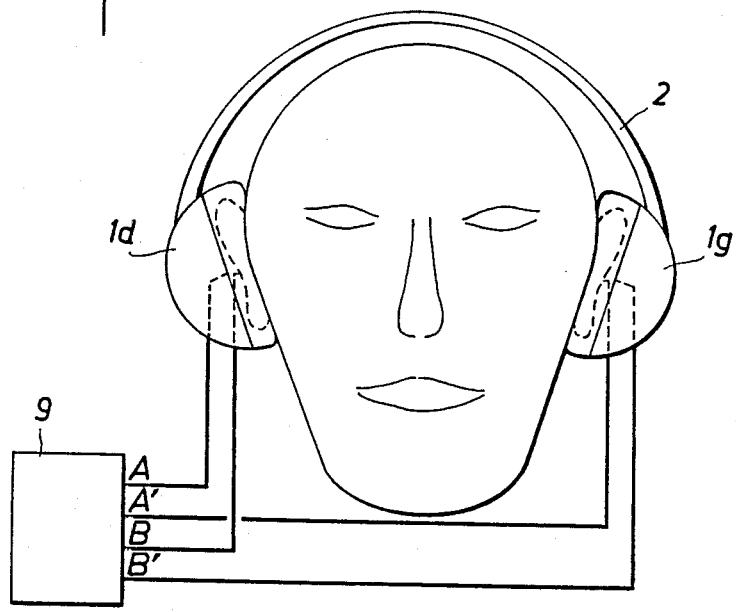
FIG. 1 is a diagrammatic overall view of soundproofing apparatus in accordance with the invention.
Figure 4:
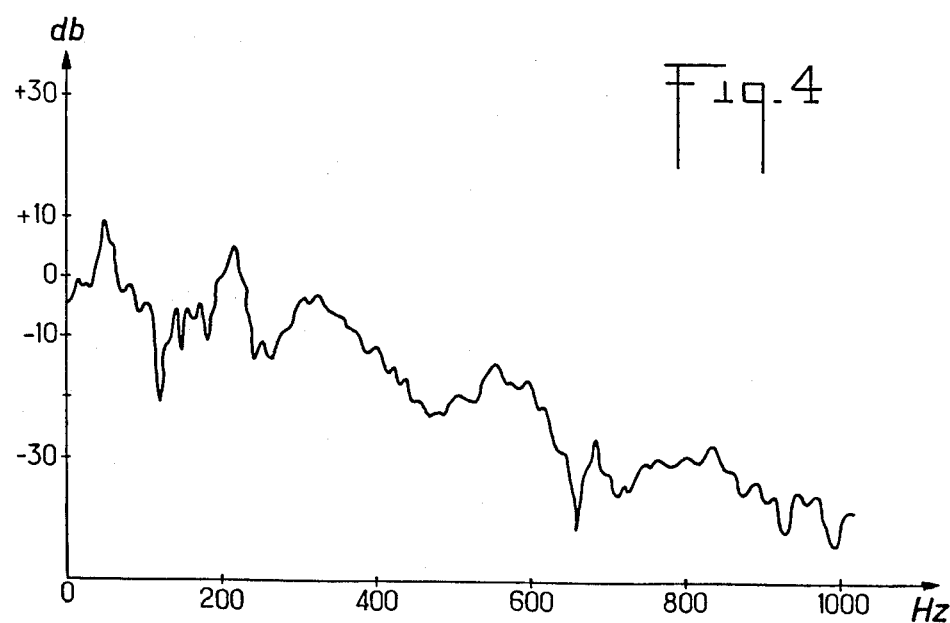
FIG. 4 is a graph showing the modulus of the sound spectrum inside a given passive headset when the external noise is white noise.

FIG. 4 is a graph with sound frequency plotted along the X axis and with the modulus of the transfer function plotted along the Y axis, for the case of a microphone placed inside a passive muff as shown in FIG. 1 and external white noise.

It is recalled that the transfer function $H(w)$ is a complex function expressing the ratio between the Fourier transform $S(w)$ of a signal leaving a device and the Fourier transform $E(w)$ of the signal applied to the input to said device, i.e. $H(w)=S(w)/E(w)$.

FIG. 4 thus shows the noise level in relative decibels as measured inside the cavity delimited by one of the muffs 1d or 1g at each frequency contained in the external noise. It can be seen that at frequencies below 600 Hz, the attenuation obtained is less good than at higher frequencies.

The problem to be solved is to add active soundproofing means to passive soundproofing apparatus in order to provide attenuation mainly at those frequencies which escape from the passive attenuation, given that the active means may also improve attenuation at higher frequencies that are already attenuated by the passive means.

Figure 2:
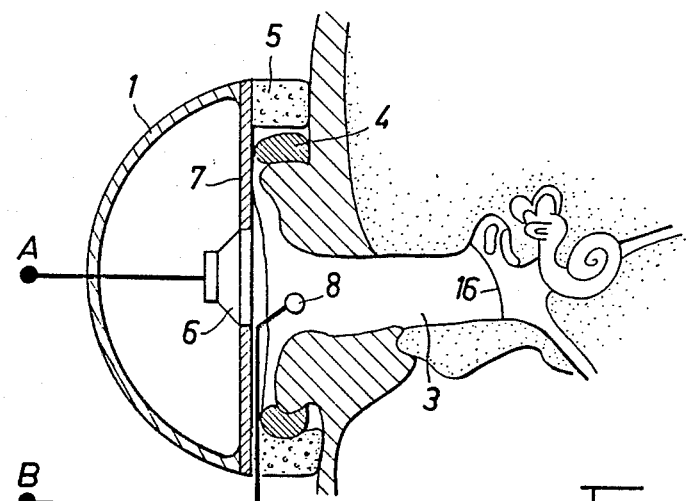
FIG. 2 is a section through an ear fitted with apparatus in accordance with the invention.

FIG. 2 is a section through an ear showing the external ear duct 3, the eardrum 16 and the pinna 4 placed inside an insulating muff 1 including a lining 5 of cellular material which is pressed against the skin around the pinna.

FIG. 2 shows an electro-acoustic transducer 6, e.g. a small loudspeaker, which is supported by a partition 7 fixed on the insulating muff 1. The emitting face of the loudspeaker 6 is directed towards the ear. It is placed substantially opposite the opening to the external ear duct 3 and preferably at a short distance from said opening, e.g. at a distance of about a few centimeters. The transducer 6 is connected by an electrical conductor to a terminal A.

FIG. 2 also shows a microphone 8 which is disposed inside the external ear duct 3 or between the emitting face of the loudspeaker 6 and the inlet to said duct 3, and which is connected via a conductor to a terminal B.

FIG. 1 shows a housing 9 which contains the electronic components and the circuits respectively connecting terminal A to terminal B for one of the ears and terminal A' to B' for the other ear.

Figure 3:
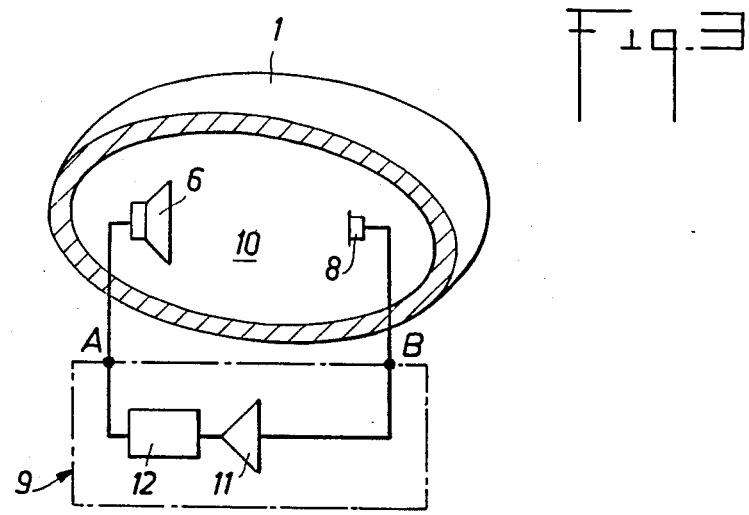
FIG. 3 is a diagram of the components of apparatus in accordance with the invention.

FIG. 3 is a theoretical diagram showing a section through the closed cavity 10 corresponding to coupling the open cavity of the muff with the open cavity of the ear, and in which an electro-acoustic transducer 6 and a microphone 8 are placed. The microphone 8 is connected to the transducer 6 via an electronic circuit comprising an amplifier 11 having constant gain K and an active type of analog filter 12, i.e. a filter comprising selective amplifiers associated with passive components (capacitors or resistors).

FIG. 3 shows the terminals A and B visible in FIGS. 1 and 2.

Interference takes place in the external ear duct between two opposing acoustic pressures.

The first pressure is due to noise coming from the outside through the muff 1 and attenuated to a greater or lesser extent depending on its frequency. After applying the Fourier transform, this acoustic pressure may be represented by a complex function $Po(w)$ where w is the angular frequency corresponding to each frequency f (i.e. $w=2\pi f$).

The second pressure is a pressure resulting from the waves emitted by the transducer 6 on the basis of signals emitted by the microphone 8, as amplified by the amplifier 11 and transformed by the filter 12. The circuit running from the microphone via the amplifier, the filter, and the loudspeaker, and returning to the input of the microphone constitutes a feedback loop which is closed within the external ear.

Let $P(w)$ designate the complex function representing the Fourier transform of the resulting pressure.

Let K designate the constant gain of the amplifier.

Let $H(w)$ designate the open loop transfer function between points A and B.

Let $C(w)$ designate the transfer function of the filter 12.

Given that the feedback loop is closed, the total pressure $P(w)$ may be written, using the Fourier transforms, as being equal to the sum of the incident pressure $Po(w)$ and the pressure due to the feedback which is equal to: $K.H(w).C(w).P(w)$.

This gives rise to the following equations:

$$P(w)=Po(w)+K.H(w).C(w).P(w) \qquad (1)$$

whence $$P(w)/Po(w)=1/(1-K.H(w).C(w)) \qquad (2)$$

This equation shows that the acoustic pressure $P(w)$ reaching the ear may be attenuated over a given frequency range if the ratio $P/Po$ can be reduced throughout this range, i.e. if it is possible to obtain a value for the complex product $K.H(w).C(w)$ which is much greater than unity, while nevertheless avoiding resonance phenomena at certain frequencies.

There would be no point in attenuating noise over a range of frequencies if this were also to give rise to even more inconvenient interfering noise due to the howl-around effect.

An examination of equation (2) shows that if it is possible to provide a filter having a transfer function $C(w)=H^{-1}(w)$ over the entire given frequency range, then all that would be required would be an amplifier having a gain K which is very high in order to obtain very good noise attenuation over the frequency range.

It is possible to approximate to a transfer function which is the inverse of the open loop transfer function by using digital filters associated with a processor unit, however this solution is bulky, expensive, and is not capable of working in real time as is required by the feedback system.

The filter 12 used in the apparatus shown in FIGS. 1 to 3 is an analog filter which is small and cheap, and which is not capable of providing a transfer function which is the inverse of the open loop transfer function.

The open loop transfer function H(w) may be measured by omitting the housing 9 and applying an electrical input signal to terminal A corresponding to white noise and by picking up from B the output electrical signal emitted by the microphone 8.

These two input and output electrical signals should be then simultaneously applied to a spectrum analyzer programmed to perform analog-to-digital conversion on both signals and to compute the open loop transfer function H(w) corresponding to discrete frequencies.

The spectrum analyzer includes a screen on which it displays, as a function of frequency, both the phase of the transfer function and the variations in its modulus.

Spectrum analysis shows that the open loop transfer function, i.e. the ratio between the Fourier transform of the output signal at point B and the input signal at point A depends largely on the shape and the volume of the cavity 10 and also on the respective positions of the transducer 6 and the microphone 8 relative to the cavity.

Laboratory studies have shown that the phase shifts and the variations in the modulus of the open loop transfer function can be reduced.

Instead of using the open loop transfer function H(w) directly, this transfer function may be optimized prior to electronic processing. Optimizing a transfer function which exists in a feedback loop makes it possible to obtain greater active acoustic attenuation over a wider frequency range. Optimizing the open loop transfer function comes to the same as performing "pseudo-linearization" thereof, such that the modulus and the phase of H(w) are constant and the phase shift is small over the range of frequencies to be attenuated in accordance with the principle of the invention. Thus the greater the extent to which the transfer function H(w) is "linear" the more the electronic processing for the feedback is simplified.

The method proposed for optimizing the open loop transfer function H(w) consists in a series of steps. First, the cavity 10 is subdivided into two cavities by means of a partition 7 (cf FIGS. 2 and 3, for a loudspeaker having little or no baffling) such that the "front cavity" corresponds to the assembly constituted by items 3, 4, 5, 6, 7, and 16, while the "rear cavity" corresponds to the assembly formed by items 1, 6, and 7. The microphone 8 is then placed in the above-described "front cavity" either in front of the loudspeaker and close to the inlet to the external ear duct, or else inside the duct. The microphone is then placed at a short distance from the loudspeaker in order to reduce phase shift, and the volume of the cavity 10 is reduced as much as possible in order to avoid resonance and anti-resonance effects.

In practice, since the open loop transfer function H(w) may be quite different depending on the geometrical shape of the enclosure 10 and on the positions of the transducer 6 and of the microphone 8, any improvement to the soundproofing provided by a passive muff 1 of given shape and nature by means of an active system begins by determining and fixing the positions of the transducer 6 and the microphone 8 inside the muff 1, and then in using a spectrum analyzer to measure the open loop transfer function H(w) of this set of items when placed on an ear.

Figure 7:
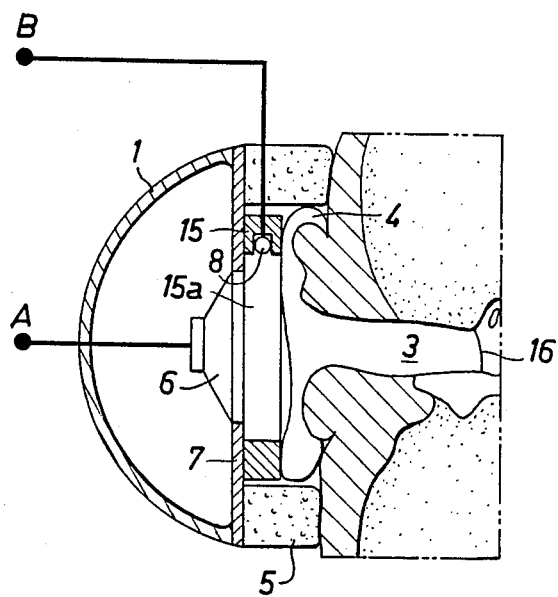
FIG. 7 is a section through an ear fitted with apparatus in accordance with the invention.

FIG. 7 is a diagrammatic section through another embodiment of apparatus in accordance with the invention. Parts which are equivalent to parts of FIG. 2 have been given the same references.

In the FIG. 7 embodiment, an annular part 15 delimiting an intermediate cavity 15a is interposed between the partition 7 and the ear pinna 4 inside the lining 5. Advantageously, this part 15 serves as a support for the microphone 8 which may be disposed in a hollow in the part 15 as shown in FIG. 7, or which may be juxtaposed with said part 15.

Depending on the ranges of frequencies to be attenuated, the open loop transfer function H(w) may be optimized by means of acoustic filtering. For example, if low frequencies are to be attenuated, an annular part 15 fixed against the partition 7 provides acoustic filtering by a cavity effect. In the FIG. 7 example, the ratios of the diameters, the thicknesses, the aperture of the screen (baffle) 7 of the annular part 15, and of the external ear duct 3 define a low-pass acoustic filter. It is thus possible to model the transfer function H(w) by calculating and performing acoustic prefiltering prior to electronic processing.

The dimensions of the intermediate part 15 and of the intermediate cavity 15a delimited thereby are determined so that the ratio between the dimensions of said intermediate cavity and of said front and rear cavities separated by the partition 7 give rise to acoustic filtering having a pass band corresponding to the range of frequencies to be attenuated.

Preferably, the active face of the microphone faces towards the emissive face of the loudspeaker in order to optimize the open loop transfer function H(w).

Once the transfer function H(w) has been established, the filter 12 is designed to provide a transfer function C(w) such that the product of the constant gain K of the amplifier 11 multiplied by the modulus of the open loop transfer function H(w) and by the modulus of the transfer function C(w) of the filter 12 is much greater than unity within the range of frequencies over which an improvement in external noise attenuation is desired. This condition is not sufficient. It is also necessary to verify that the stability criterion is satisfied in order to avoid "howlaround" phenomena which would lead to the production of noise by virtue of resonance at certain frequencies (the Larsen effect).

In order to avoid howlaround due to resonance, it is necessary for the Nyquist stability criterion to be satisfied as is well known to the person skilled in electrical art. It is briefly recalled that the Nyquist criterion consists in verifying on a so-called Nyquist plot that the overall transfer function F(w) of all of the items in a system does not intersect the real axis at a point greater than unity for all of the frequencies in the spectrum being listened to.

The Nyquist plot has the real portion of the transfer function plotted along the X axis and the imaginary portion plotted along the Y axis.

Let F(w) be the overall open loop transfer function of the system.

Let $|F(w)|$ be the modulus and $\phi(w)$ be the phase of said function.

Let $\Delta\phi$ be the phase stability margin and $\Delta\rho$ be the modulus stability margin.

The phase stability margin $\Delta\phi$ corresponds to the amount, in radians, by which the phase of the transfer function F(w) may vary due to unforeseeable interference delays without the system becoming unstable.

The modulus stability margin $\Delta\rho$ corresponds to the amount of unforeseen variation in the modulus of the transfer function F(w) which can be tolerated in the feedback system without it becoming unstable.

It has been shown that active acoustic attenuation is obtained over a range of frequencies wi by means of an electro-acoustic feedback loop without giving rise to an unstable system because of resonance if, and only if:

$$|F(wi)| > 1 - \Delta \rho$$

and $$2K\pi + \Delta\phi < (wi)2K\pi - \Delta\phi \text{ for } K=0,1,2,\ldots$$

If $$|F(wi)| \leq 1 - \Delta \rho$$

then the system provides no active attenuation, in which case the system is stable regardless of the value of the phase $\phi(w)$.

Providing both conditions are satisfied, those acoustic waves which are not stopped by the passive soundproofing apparatus 1 and which reach the inlet to the external ear interfere with acoustic waves emitted by the loudspeaker 6, and this interference minimizes the ratio P/Po between the modulus P of the resulting acoustic wave and the modulus Po of the incident acoustic wave over the entire range of frequencies for which the product $K.|H(w)|.|C(w)|$ is much greater than unity. In addition there are no interfering sounds due to howlaround.

In practice, the filter 12 used is preferably an active analog filter comprising, for example, one or more integrated circuit filters each having a polynomial transfer function of the form:

$$C(w) = (a1(w)^2 + a2(w) + a3)/(b1(w)^2 + b2(w) + b3).$$

Such a filter includes resistors and/or capacitors capable of being connected to the terminals of the integrated circuit and whose values are adjustable in order to obtain predetermined values for the real constant coefficients a1, a2, a3, b1, b2, and b3 of the function C(w).

The calculations necessary for constructing polynomial filters and the forms of the transfer functions of such filters are well known to persons skilled in the electrical art.

In general, the coefficients of the denominator b1, b2, and b3 are fixed in advance and they determine the cutoff frequency and the Q factor of the filter, while the coefficients a1, a2, and a3 of the numerator are varied in order to determine the nature of the filter.

If a1 and a2 are equal to zero and a3 is different from zero, a low pass filter is obtained which is advantageous since it provides a transfer function having a large modulus at low frequencies. However, such a filter gives rise to phase rotation which passes simultaneously through 0° and through ±180° at a frequency which is less than the cutoff frequency where the modulus $|C(w)|$ is > 1, thereby giving rise to howlaround which happens in the present case at 0° if K is positive.

If a2 and a3 are zero and a1 is not zero, a high pass filter is obtained which is not advantageous since the sounds which most require attenuating are low or medium frequency sounds.

If a1 and a3 are zero and a2 is not zero, a pass band filter is obtained which introduces phase rotation, e.g. from ±90° to ±90° without going through 0°, and through ±180° when the modulus of the filter, i.e. $|C(w)|$ is at its maximum, which is advantageous since there is no danger in the present system of that giving rise to howlaround.

In practice, when it is mainly low frequency sounds that are to be attenuated, it is preferable to use a mixture of filter types combining the effects of a bandpass filter and of a low-pass filter. It is also possible to associate a plurality of mixed type polynomial filter circuits (combining high-pass, low-pass, and bandpass types) in parallel or to associate bandpass filters only.

FIG. 9 shows three filters 12a, 12b, and 12c connected in parallel. Filter 12a is a lowpass filter, filter 12b is a bandpass filter, and filter 12c is a high pass filter. Preferably, filters 12a, 12b, and 12c have the same cut off frequency and the same Q factor.

Figure 5:
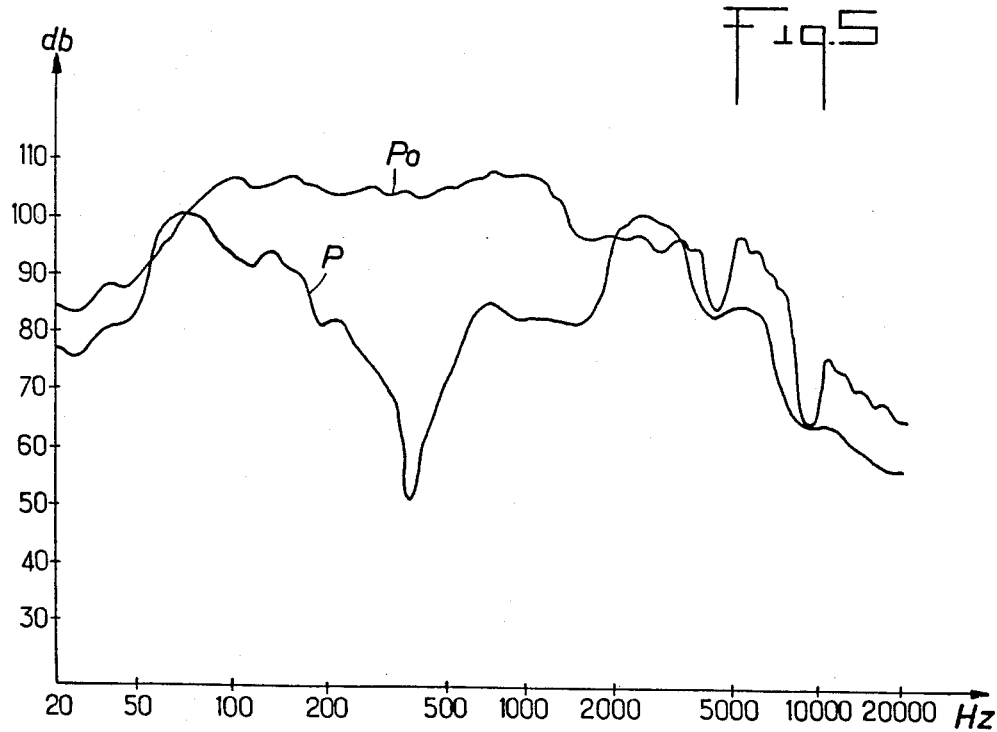
FIG. 5 is a graph showing the attenuation obtained using a device in accordance with the invention.

FIG. 5 is a graph having audible frequencies plotted in logarithmic co-ordinates along the X axis and having acoustic pressure levels plotted in decibels along the Y axis. The solid line curve Po represents the spectrum of acoustic pressure Po measured when using only a passive soundproofing headset which attenuates frequencies less than 1500 Hz poorly. The dot-dashed curve P represents the acoustic pressure spectrum measured when using the same headset in association with an active attenuator in accordance with the invention. In this case the electronic circuit used is a single active analog filter of the bandpass type.

The acoustic pressures were measured in the presence of white noise emitted by a loudspeaker enclosure over the frequency range 20 Hz to 20,000 Hz. The acoustic pressures are measured by means of a small microphone which is inserted into the external ear as close as possible to the eardrum and they thus represent the sounds actually perceived by the ear. The spectra Po and P are obtained by means of a spectrum analyzer which applies a Fourier transform to the measurements.

The FIG. 5 graph shows average results measured over very many tests. This graph shows that attenuation lying between 0 dB and 8 dB is obtained in the frequency band 20 Hz to 55 Hz, with very good attenuation lying between 0 dB and 50 dB being obtained in the frequency band from 65 Hz to 2000 Hz, and with slight attenuation being obtained between 3800 Hz and 20,000 Hz.

There are two narrow frequency bands between 55 Hz and 65 Hz and between 2000 Hz and 3800 Hz in which there is no attenuation and in which there is even a slight increase in noise level, which increase remains below 6 dB.

Advantageously, a plurality of bandpass filters are connected in parallel in the feedback loop, for example second or third order filters having juxtaposed pass bands which cover the major portion of the frequency range in which open loop phase rotation of the system including the filters satisfies Nyquist stability criterion.

FIG. 8 shows filter means comprising 2 analog filters 12a and 12b connected in parallel. Filters 12a and 12b can be bandpass filters. Alternatively, filter 12a can be a lowpass filter and 12b can be a bandpass filter.

This parallel connection of a plurality of filters has the advantage of enabling the individual pass bands of the filters to be added together while giving rise to phase rotation which is the average of the phase rotations of the individual filters and which thus remains between −90° and −270° for second order filters and between −45° and −315° for third order filters, i.e. within regions satisfying the Nyquist stability criterion.

In a preferred example, a bandpass filter is used in conjunction with a high-pass filter having the same cutoff frequency and the same Q factor.

This result is obtained by using an integrated circuit in association with variable resistors which can be adjusted to set the three coefficients a1, a2, and a3 of the numerator of the polynomial transfer function.

It is thus possible to obtain either a predominantly bandpass filter by giving more weight to the coefficient a2 relative to the other two coefficients a1 and a3, or else to relative to the other two coefficients a1 and a3, or else to obtain a predominently low pass filter by giving more weight to the coefficient a3.

The effect of the high-pass filter contained in such a compound filter is to reduce phase rotation and to make it tend towards zero at high frequencies without substantially altering the appearance of the modulus, thereby enabling the width of the attenuation passband to be enlarged towards high frequencies without introducing instability and thus increasing the attenuation and the width of the attenuated band.

Instead of associating three filters having the same cutoff frequencies and the same Q factors, it is also possible to connect a plurality of low-pass, bandpass, and high-pass filters having different cutoff frequencies such that the lowest cutoff frequency is that of the high-pass filter and the highest cutoff frequency is that of the low-pass filter, and with the filters having different Q factors.

This association gives rise to sharper edged pass bands than the previous association with phase rotation tending towards zero outside the pass band, it also gives rise to higher frequencies in the low frequency range.

All of these adjustments can be performed by initially performing digital simulation using the measured open loop transfer function H(w) and by manually adjusting the variable resistors as needed in order to determine the optimum transfer function C(w) of the filter.

All of these examples clearly show the wide range of possibilities offered by the method in accordance with the invention for obtaining high performance active sound attenuators which may be implanted in existing soundproofing headsets or in headsets which have been specially designed to receive such attenuators.

Curve P1 of FIG. 5 shows an example of the attenuation curve obtained by associating a plurality of second order analog filters of the low-pass, bandpass, and high-pass types in parallel with different cutoff frequencies and with different Q factors. It can be seen that attenuation is obtained over a frequency band which is wider than that shown by curve P and that the peaks for which noise level is increased are eliminated.

Very often, sound insulating headsets include an incorporated loudspeaker in order to transmit messages to the user by electro-acoustic means.

If a headset in accordance with the invention including an active attenuator is fitted with a second loudspeaker which is not included in the feedback loop and which is intended for transmitting messages, sounds emitted by the second loudspeaker are considered as sounds coming from the outside and are therefore picked up by the microphone and by the feedback loop and are attenuated. This solution must therefore be avoided.

Another solution consists in applying the electrical signals conveying the message directly to the loudspeaker 6 which forms a part of the active attenuator.

Equations and practice show that such a circuit enables a message to be heard even though the message is distorted by the feedback. However, there is a better circuit.

Figure 6:
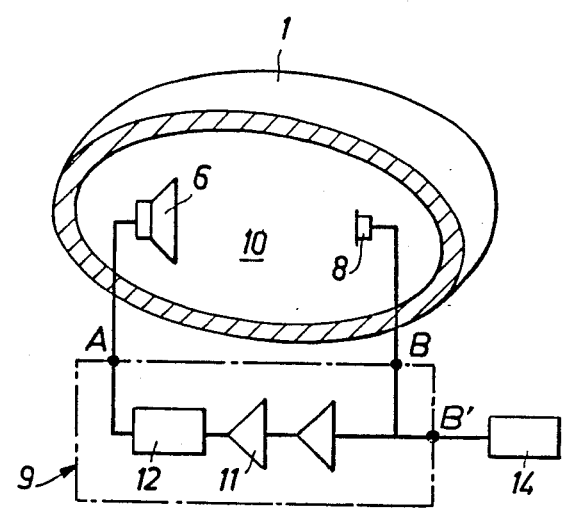
FIG. 6 is a diagram showing the components of a device in accordance with the invention for enabling messages to be heard as transmitted over an electro-acoustic path.

FIG. 6 is a diagram similar to FIG. 3 and shows this circuit. Portions thereof equivalent to portions of FIG. 3 are given the same references.

The housing 9, in addition to the constant gain amplifier 11 and the filter 12 also contains a summing circuit 13 which receives firstly the signals from the microphone 8 and secondly electric signals from an external transducer 14 for conveying a message.

Experience shows that such a circuit makes it possible not only to attenuate the noise reaching the eardrum without attenuating the level of the message, but also to escape from the transfer function of the loudspeaker 6 and of the cavity 10 over the range of frequencies under consideration.

In the following equations, K, C(w), Po(w), Pt(w) and H(w) have the same meanings as in equations (1) and (2).

The open loop transfer function H(w) between points A and B may be decomposed into a product of a first transfer function H1(w) between point A and the input to the microphone multiplied by a second transfer function H2(w) which is the transfer function of the microphone. In practice, the modulus of the microphone transfer function may be substantially constant over a wide frequency band providing the microphone is of good quality.

Let Sp(w) designate the Fourier transform of the electric signal emitted by the external transducer 14 for conveying the message.

The following equation may then be written:

$$Pt(w) = (K.H1(w).C(w).Sp(w) + Po(w))/(1 - K.H(w).C(w)) \quad (3)$$

If the gain K of the amplifier is very large, then:

$$Pt(w) \simeq Sp(w).(H1(w)/H(w)) + \epsilon \simeq Sp(w).H2(w) + \epsilon \quad (4)$$

Equation (4) shows that the FIG. 6 circuit serves both to attenuate the residue of external origin noise by virtue of the feedback loop while simultaneously improving hearing of the message which is no longer subjected to the transfer function H1(w) which represents the transfer function of the combination of the cavity and the loudspeaker.

The FIG. 6 circuit can be used to provide a kind of feedback loop filtering of a message which is mixed with external noise.

If the response of the microphone 8 is considered as being ideal, i.e. H1(w)≃H(w), then equation (4) becomes:

$$Pt(w) \simeq Sp(w) + \epsilon.$$

The suggested circuit does not reduce the level of the message Sp(w) which is thus not only reinstated intact, but in addition, it is freed from any transfer function, and this would not be the case if the signal leaving the transducer 14 were applied directly to the loudspeaker 6.

It can thus be seen that the solution in accordance with FIG. 6 makes it possible to hear a message sent electro-acoustically and transmitted via the same transducer 6 used by the active attenuator after increasing its level relative to the level of outside noise and also improving the message by virtue of the fact that the transfer function H1(w) which inevitably appears in any other circuit is eliminated.

Equations and experimental measurements show that any other position for the summing circuit in the feedback loop does not improve the intelligibility of the message by "feedback filtering" and leads to degradation of the intelligibility of the transmitted message, which degradation can sometimes be very high. The intelligibility of the message can be further improved in accordance with the FIG. 6 circuit providing the range of frequencies to be attenuated is centered on the speech band 300 Hz to 3000 Hz. This range of frequencies corresponds to the most sensitive region of the human ear, and thus when active attenuation is being used above all for improving message intelligibility, it is no longer necessary to provide high attenuation at low frequencies as is the case when providing protection only without communication. Indeed, it becomes necessary to improve passive attenuation from 300 Hz by broadening as much as possible the range of attenuated frequencies in order to reach 2000 Hz or better still 3000 Hz, even if some efficiency is lost in pure noise attenuation.

The above description relates above all to low and medium frequency ranges. In this case, equations show that the combination of acoustic attenuation and of "feedback filtering" of the transmitted message improves working conditions and also message intelligibility. However, it has just been shown that if the frequency range of active attenuation is centered on the speech band, i.e. 300 Hz to 3000 Hz, even if little attenuation is obtained in the high frequency zone thereof, the intelligibility of the transmitted message is better still and this effect is further improved if the range of attenuated frequencies extends up to high frequencies of the order of 2000 Hz to 3000 Hz.

Equation (3) also shows that if Po(w) is very small, the feedback filtering phenomenon of the message is retained since the second member of the equation is independent of the pressure Po(w) and the result of equation (4) for gain K large in comparison with unity is thus again satisfied, i.e. the message Sp(w) is free from any transfer function. The active acoustic absorption system can thus be used solely for improving the message by feedback loop filtering, even when external noise is not inconvenient.

The above description relates to preferred embodiments in which the filter 12 is an analog filter. However, it is specified that it would also be possible to use a digital filter on its own or in association with a processor unit, in combination with passive soundproofing apparatus when used on board a vehicle.

In a variant embodiment, an active apparatus in accordance with the invention includes a small microphone which is placed in the external ear together with a miniaturized transducer whose rear face includes a coating which constitutes a plug and which is engaged in the inlet to the external ear. In this case, the cavity is reduced to the volume delimited by the external ear, the eardrum and the transducer-carrying plug, and the open loop transfer function H(w) is highly linear so that it is easy to obtain a good level of attenuation over a wide frequency band by electronic filtering.

We claim:

1. Apparatus for attenuating externally originating noise reaching the eardrum, the apparatus being of the type including passive soundproofing means which together with each ear delimits a respective cavity, and also including an electro-acoustic transducer and a microphone disposed inside each said cavity and interconnected via a feedback loop including a constant gain amplifier and a filter with which they constitute an active sound attenuator, the apparatus being characterized in that the transfer function C(w) of said filter is a complex polynomial function and in that the product of the constant gain K of said amplifier multiplied by the modulus |C(w)| of the transfer function of said filter and by the modulus |H(w)| of the open loop transfer function as measured at the input to said transducer and at the output from said microphone is considerably greater than unity throughout the range of low audio frequencies which are to be attenuated and satisfies the stability criterion for all audible frequencies.

2. Apparatus according to claim 1, characterized in that said filter comprises one or more analog filters of the bandpass or bandpass and lowpass type which are connected in parallel and which provide a transfer function suitable for avoiding instabilities in the zone where the modulus is greatest.

3. Apparatus according to claim 1, characterized in that said filter comprises a plurality of analog filters of the low-pass, bandpass, and high-pass types, which filters are connected in parallel and have the same cut-off frequency and the same Q factor.

4. Apparatus according to claim 1, characterized in that the gain K of said amplifier is positive and in that the transfer function C(w) of said filter is determined such that the phase of said transfer function does not pass through the value zero in the pass band of said filter.

5. Apparatus according to claim 1, of the type in which each of said cavities includes a transverse partition which divides it into two half-cavities, namely a front half-cavity and a rear half-cavity, said partition carrying said acoustic transducer, and in which said microphone is disposed in said front half-cavity, the apparatus being characterized in that it further includes an annular part which is interposed between said partition and the pinna of the ear and which delimits an intermediate cavity, with the dimensions of said annular part being designed so that the ratio between the dimensions of said intermediate cavity and of said front and rear half-cavities gives rise to acoustic filtering having a pass band corresponding to the range of frequencies to be attenuated.

6. Apparatus according to claim 1, characterized in that said microphone is placed in the ear duct and said transducer is a miniaturized transducer whose covering on its rear face forms a plug which is engaged in the inlet to the external ear duct such that said cavity is reduced to the volume delimited by the ear duct, the eardrum, and the transducer, and such that the open loop transfer function H(w) is highly linear, enabling a good level of attenuation to be obtained over a wide frequency band.

7. A method of attenuating external origin noise reaching the eardrum, comprising the following steps:
placing around each ear a passive soundproofing means which, together with the ear, delimits a cavity;
placing in each of said cavities an electro-acoustic transducer and a microphone;
electrically interconnecting said microphone and said transducer by an electronic feedback loop comprising a constant gain amplifier and a filter having a transfer function which is a complex polynomial function;

measuring the open loop transfer function H(w) of the assembly constituted by the transducer, the microphone and said cavity; and calculating the coefficients of said polynomial function so that the product of the constant gain of said amplifier multiplied by the modulus of said open loop transfer function and by the modulus of the transfer function of said filter is much greater than unity over the range of low frequencies where said passive soundproofing means is of low effectiveness.

8. A method according to claim 7, including the steps of attenuating externally originating noise with active soundproofing means placed at inlets to ears, permitting a message to be transmitted via an electro-acoustic path, applying electrical signals reflecting said message mixed with signals emitted by said microphone, applying said mixed signals via said amplifier to said transducer, and passing said signals through said filter.

9. A method according to claim 7, characterized by sub-dividing said cavity into two half-cavities, a front half-cavity being delimited by the pinna of the ear, the external ear duct, the eardrum, and said partition, and a rear half-cavity delimited by said passive soundproofing means and said partition, said partition carrying said transducer, and placing said microphone in said front half-cavity as close as possible to the emissive face of said transducer.

10. A method according to claim 9, characterized by reducing the volume of said cavity as much as possible in order to "linearize" said open loop transfer function H(w).

11. A method of attenuating external origin noise reaching the eardrum, comprising the following steps:

placing around each ear passive soundproofing means which, together with the ear, delimits a cavity;

placing in each of said cavities an electro-acoustic transducer and a microphone;

electrically interconnecting said microphone and said transducer by an electronic feedback loop comprising a constant gain amplifier and a filter having a transfer function which is a complex polynomial function;

temporarily disconnecting said microphone from said transducer, applying an electric signal corresponding to white noise to the input of said transducer and measuring the open loop transfer function H(w) of the assembly constituted by said transducer, said microphone and said cavity by means of a spectrum analyzer which simultaneously receives said electrical signal and the electric signal emitted by said microphone; and calculating the coefficients of said polynomial function so that the product of the constant gain of said amplifier multiplied by the modulus of said open loop transfer function and by the modulus of the transfer function of said filter is much greater than unity over the range of low frequencies where said passive soundproofing means is of low effectiveness.

12. A method according to claim 11, further comprising the following steps:

sub-dividing said cavity into two half-cavities by a partition carrying said transducer;

interposing an annular part between said partition and the pinna of the ear; and designing the shape and dimensions of said annular part so that it performs acoustical filtering giving an open loop transfer function having a low-pass filter or a band-pass filter function depending on the range of audio frequencies to be attenuated and placing said microphone in the half-cavity situated in front of said partition as close as possible to the emissive face of said transducer.

13. A method according to claim 11, including the steps of attenuating externally originating noise with active soundproofing means placed at inlets to ears, permitting a message to be transmitted via an electro-acoustic path, applying electrical signals reflecting said message mixed with signals emitted by said microphone, applying said mixed signals via said amplifier to said transducer, and passing said signals through said filter.

14. A method according to claim 11, characterized by sub-dividing said cavity into two half-cavities, a front half-cavity being delimited by the pinna of the ear, the external ear duct, the eardrum, and said partition, and a rear half-cavity delimited by said passive soundproofing means and said partition, said partition carrying said transducer, and placing said microphone in said front half-cavity as close as possible to the emissive face of said transducer.

15. A method according to claim 14, characterized by reducing the volume of said cavity as much as possible in order to "linearize" said open loop transfer function H(w).

16. Apparatus for attenuating external origin noise reaching the eardrum comprising passive soundproofing means surrounding each ear which delimits with each ear a cavity, and further comprising an electro-acoustic transducer and a microphone which are disposed in each of said cavities and which are electrically interconnected via an electronic feedback loop including a constant gain amplifier and filter means having a complex polynomial transfer function wherein the product of the constant gain of said amplifier multiplied by the modulus of said transfer function of said filter means and by the modulus of the open loop transfer function measured between the input electric signal to said transducer and the output electric signal from said microphone is much greater than unity over the range of low audio frequencies and wherein said filter means comprises a plurality of analog filters of the low pass, band-pass and high pass types which are connected in parallel and have the same cut-off frequency and the same Q factor.

17. Apparatus for attenuating external origin noise reaching the eardrum comprising passive soundproofing means surrounding each ear which delimits with each ear a cavity, and further comprising an electro-acoustic transducer and a microphone which are disposed in each of said cavities and which are electrically interconnected via an electronic feedback loop including a constant gain amplifier and filter means having a complex polynomial transfer function wherein the product of the constant gain of said amplifier multiplied by the modulus of said transfer function of said filter means and by the modulus of the open loop transfer function measured between the input electric signal to said transducer and the output electric signal from said microphone is much greater than unity over the range of low audio frequencies, and wherein said filter means comprises one or more analog filters of the band-pass type or of the band-pass and low pass type which are connected in parallel, which have a transfer function suitable for avoiding instabilities in the zone where the modulus is greatest.

18. Apparatus according to claim 17, characterized in that said filter further includes one or more high-pass filters connected in parallel with said low-pass filters and said bandpass filters.

19. Apparatus for attenuating external origin noise reaching the eardrum comprising passive soundproofing means surrounding each ear which delimits with each ear a cavity, and further comprising an electro-acoustic transducer and a microphone which are disposed in each of said cavities and which are electrically interconnected via an electronic feedback loop including a constant gain amplifier and filter means having a complex polynomial transfer function wherein the product of the constant gain of said amplifier multiplied by the modulus of said transfer function of said filter means and by the modulus of the open loop transfer function measured between the input electric signal to said transducer and the output electric signal from said microphone is much greater than unity over the range of low audio frequencies and wherein the gain of said amplifier is positive and the transfer function of said filter means is determined such that the phase of said transfer function does not pass through the value zero in the pass-band of said filter means.

* * * * *

US004833719C1

(12) EX PARTE REEXAMINATION CERTIFICATE (7570th)
United States Patent
Carme et al.

(10) Number: US 4,833,719 C1
(45) Certificate Issued: Jun. 29, 2010

(54) METHOD AND APPARATUS FOR ATTENTUATING EXTERNAL ORIGIN NOISE REACHING THE EARDRUM, AND FOR IMPROVING INTELLIGIBILITY OF ELECTRO-ACOUSTIC COMMUNICATIONS

(75) Inventors: Christian E. Carme, Marseille (FR);
Alain R. Roure, Marseille (FR)

(73) Assignee: Centre National de la Recherche Scientifique, Paris (FR)

Reexamination Request:
No. 90/007,841, Dec. 12, 2005

Reexamination Certificate for:
Patent No.: 4,833,719
Issued: May 23, 1989
Appl. No.: 07/110,699
Filed: Sep. 23, 1987

(51) Int. Cl.
*A61F 11/00* (2006.01)
*A61F 11/14* (2006.01)
*G10K 11/00* (2006.01)
*G10K 11/178* (2006.01)

(52) U.S. Cl. .......................................... 381/72; 381/71.6
(58) Field of Classification Search .................... 360/46;
381/74; 361/154

See application file for complete search history.

(56) References Cited

U.S. PATENT DOCUMENTS

| 3,628,102 A | * | 12/1971 | Jauch et al. | 361/154 |
| 4,494,074 A | | 1/1985 | Bose | |
| 4,609,951 A | * | 9/1986 | Aruga | 360/46 |
| 4,644,581 A | * | 2/1987 | Sapiejewski | 381/74 |

OTHER PUBLICATIONS

Sedra et al., "Microelectronic Circuits," *CBS College Publishing*, New York, 1982.
Wheeler et al., "An Active Noise Reduction System for Aircrew Helmets," *AGARD Conference Proceedings No. 311*, Mar. 30–Apr. 2, 1981.

* cited by examiner

*Primary Examiner*—Christopher E Lee

(57) ABSTRACT

The invention relates to a method and to apparatus for attentuating externally originating noise reaching the eardrum while still enabling communication via an electro-acoustic path. Apparatus according to the invention comprises passive attenuation means disposed about each ear and delimiting a cavity (10). In addition it includes active attenuation means comprising a loud-speaker (6) placed inside the cavity (10) and a microphone (8) placed in the external ear duct or at the inlet thereto, said loudspeaker and microphone being inter-connected by a constant gain amplifier (11) and an active analog filter (12) of the polynomial type, with the passive components thereof being designed to provide a given transfer function. One application lies in the construction of protective headsets fitted with incorporated loudspeakers enabling electro-acoustic communication.

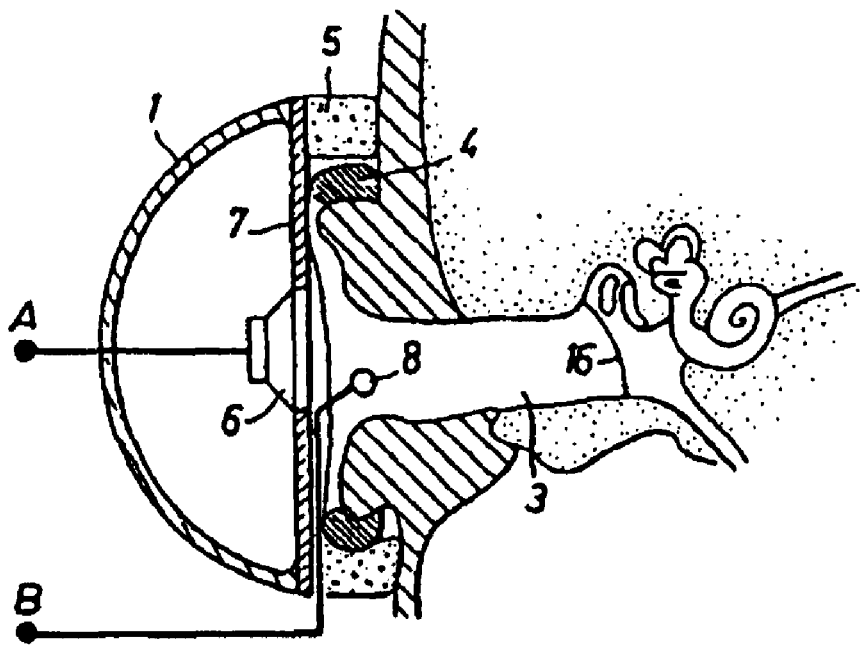

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-19 is confirmed.

* * * * *